(12) United States Patent
Martin et al.

(10) Patent No.: US 7,468,452 B1
(45) Date of Patent: Dec. 23, 2008

(54) PROCESS FOR ONE-POT SYNTHESIS OF 1,1-DIPHENYL-1-(3-SUBSTITUTED-CYCLOPENTADIENYL)-1-(2,7-DI-T-BUTYL-FLUOREN-9-YL)METHANE TYPE LIGANDS

(75) Inventors: Joel L. Martin, Bartlesville, OK (US); Albert P. Masino, Tulsa, OK (US); Qing Yang, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 12/001,733

(22) Filed: Dec. 12, 2007

(51) Int. Cl.
*C07F 17/00* (2006.01)
*C07F 7/00* (2006.01)
*B01J 31/00* (2006.01)
*C08F 4/44* (2006.01)

(52) U.S. Cl. .............................. 556/53; 556/11; 556/12; 526/160; 526/943; 502/103

(58) Field of Classification Search .................... 556/11, 556/12, 53
See application file for complete search history.

(56) References Cited

U.S. PATENT DOCUMENTS

| 5,416,228 | A * | 5/1995 | Ewen et al. | 556/7 |
| 5,449,651 | A * | 9/1995 | Reddy et al. | 502/117 |
| 2007/0179044 | A1 | 8/2007 | Yang et al. | 502/103 |
| 2007/0197374 | A1 | 8/2007 | Yang et al. | 502/103 |

OTHER PUBLICATIONS

Kaminsky et al., Journal of Organometallics, vol. 684, pp. 200-205 (2003).*

Alt, Helmut G., et al., $C_1$-Bridged fluorenylidene cyclopentadienylidene complexes of the type ($C_{13}H_8$-$CR^1R^2$-$C_5H_3R$)$ZrCl_2$($R^1$, $R^2$=alkyl, phenyl, alkenyl; R=H, alkyl, alkenyl, substituted silyl) as catalyst precursors for the polymerization of ethylene and propylene, *Journal of Organometallic Chemistry*, 568, 1998, 87-112.

Miller, Stephen A., et al., Highly Stereoregular Syndiotactic Polypropylene Formation with Metallocene Catalysts via Influence of Distal Ligand Substituents, *Organometallics*, 2004, 23, 1777-1789.

* cited by examiner

*Primary Examiner*—Porfirio Nazario Gonzalez
(74) *Attorney, Agent, or Firm*—Merchant & Gould, P.C.

(57) ABSTRACT

The present invention is directed to a method of making a ligand which can be used to form an ansa-metallocene. Further, the present invention is directed to a method of making the ansa-metallocene. In both methods the process steps employed to form the ligand are conducted in the presence of tetrahydrofuran, a substituted tetrahydrofuran, tetrahydropyran, a substituted tetrahydropyran or ethylene glycol dimethyl ether.

12 Claims, 6 Drawing Sheets

PROCESS FOR ONE-POT SYNTHESIS OF 1,1-DIPHENYL-1-(3-SUBSTITUTED-CYCLOPENTADIENYL)-1-(2,7-DI-T-BUTYL-FLUOREN-9-YL)METHANE TYPE LIGANDS

TECHNICAL FIELD OF THE INVENTION

This invention relates to the field of organometal compositions, olefin polymerization catalyst compositions, and methods of making such organometal and catalyst compositions.

BACKGROUND OF THE INVENTION

It is known that mono-1-olefins (α-olefins), including ethylene, can be polymerized with catalyst compositions employing titanium, zirconium, vanadium, chromium, or other metals, often combined with a solid oxide and in the presence of cocatalysts. These catalyst compositions can be useful for both homopolymerization of ethylene, as well as copolymerization of ethylene with comonomers such as propylene, 1-butene, 1-hexene, or other higher α-olefins. Therefore, there exists a constant need to develop new methods of making and using olefin polymerization catalysts.

An example of this need is seen in the manufacture of bridged or ansa-metallocene catalysts. In general, ligands for ansa-metallocenes are prepared by following a multi-step synthesis. Clearly, it would significantly reduce metallocene preparation cost if the synthetic approach of the corresponding ligands could be simplified. Alt et al., *J. Organomet. Chem.* 1998, 568, 87-112 (Alt et al.), which is incorporated herein in its entirety by reference, reported a synthesis method for the ligands for certain ansa-metallocenes. The greatest advantage of this method is that fewer synthetic and isolation steps are employed as compared to the multi-step approach. In addition, it is more convenient to prepare different analogs with different substituents on the cyclopentadienyl ring via the one-pot synthesis. Unfortunately, the method described by Alt et al. does not readily produce ligands of the form $C_{13}H_8$—$CR^1R^2$—$C_5H_3R^3$, where $R^1$ and $R^2$ are phenyl or substituted phenyl, $R^3$ is alkyl, alkenyl, or substituted silyl. Thus, there exists a need for a one-pot synthesis for such ligands in the manufacture of metallocenes. Accordingly, the present invention is directed to that need.

SUMMARY OF THE INVENTION

This invention encompasses methods for preparing catalyst compositions. Useful metallocenes in preparing the catalyst compositions of this invention are directed to ansa-metallocenes that comprise a pendant alkenyl (olefin-containing) group or a pendant alkyl group attached to at least one of the cyclopentadienyl-type moieties of the bridged ligand, and also comprises two phenyl groups bonded to the bridging atom of the bridged ligand.

In accordance with the present invention, ligands or compounds of structure (I), below, are employed to make the ansa-metallocenes. Compounds of structure (I) are made using the following method, which comprises:

reacting

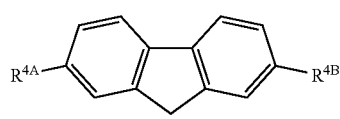

with a lithium compound in the presence of tetrahydrofuran, an alkyl or aryl substituted tetrahydrofuran, tetrahydropyran, an alkyl or aryl substituted tetrahydropyran or ethylene glycol dimethyl ether to form (Compound 1)

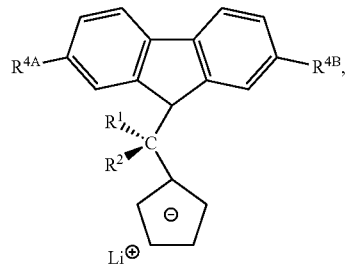

reacting Compound 1 with

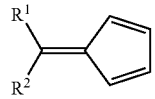

in the presence of tetrahydrofuran, an alkyl or aryl substituted tetrahydrofuran, tetrahydropyran, an alkyl or aryl substituted tetrahydropyran or ethylene glycol dimethyl ether to form (Compound 2)

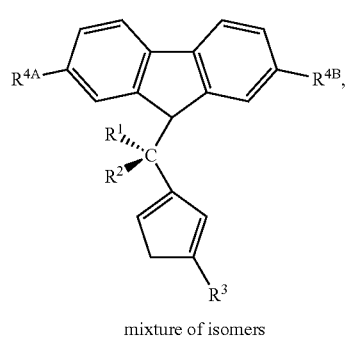

and reacting Compound 2 with $R^3X$ to form the compound of structure (I), (I)

mixture of isomers wherein:
  $R^1$ and $R^2$ are independently a substituted or unsubstituted phenyl group;
  $R^3$ is an alkyl, an alkenyl or a substituted silyl, any of which having up to 20 carbon atoms;

$R^{4A}$ and $R^{4B}$ are independently a hydrocarbyl group having up to 12 carbon atoms, or hydrogen;

X is fluorine, chlorine, bromine, iodine, or para-toluenesulfonate.

In another aspect of the present invention, a method of making an ansa-metallocene comprises:

reacting

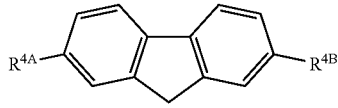

with a lithium compound in the presence of tetrahydrofuran to form

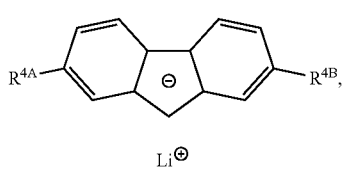

(Compound 1)

reacting Compound 1 with

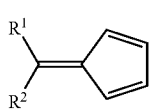

in the presence of tetrahydrofuran to form (Compound 2)

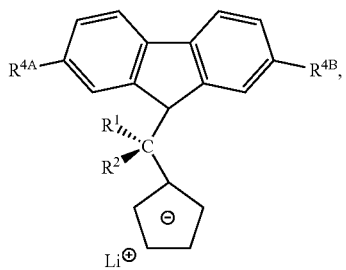

reacting Compound 2 with $R^3X$ to form the compound of structure (I):

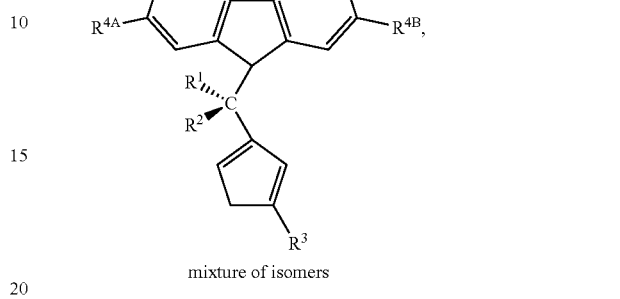

(I)

mixture of isomers and reacting the compound of structure (I) with butyllithium to form the dianion (I-dianion).

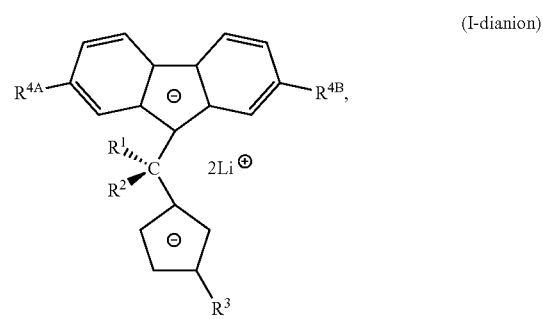

(I-dianion)

Reacting the dianion (I-dianion) with $MCl_4$ to form metallocene (M-I):

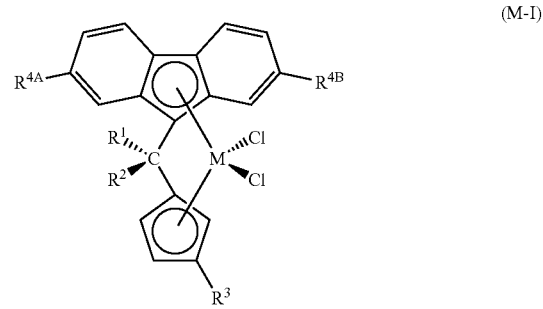

(M-I)

wherein:

$R^1$ and $R^2$ are independently a substituted or unsubstituted phenyl group;

$R^3$ is an alkyl, an alkenyl or a substituted silyl, any of which having up to 20 carbon atoms;

$R^{4A}$ and $R^{4B}$ are independently a hydrocarbyl group having up to 12 carbon atoms, or hydrogen;

X is fluorine, chlorine, bromine, iodine, or para-toluenesulfonate;

M is Zr or Hf.

DETAILED DESCRIPTION OF THE INVENTION

The instant invention is directed to a method of making metallocene having the following structure:

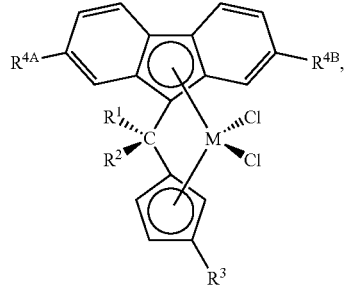

wherein:

$R^1$ and $R^2$ are independently a substituted or unsubstituted phenyl group;

$R^3$ is an alkyl, an alkenyl or a substituted silyl, any of which having up to 20 carbon atoms;

$R^{4A}$ and $R^{4B}$ are independently a hydrocarbyl group having up to 12 carbon atoms, or hydrogen;

M is Zr or Hf

Figure 1:
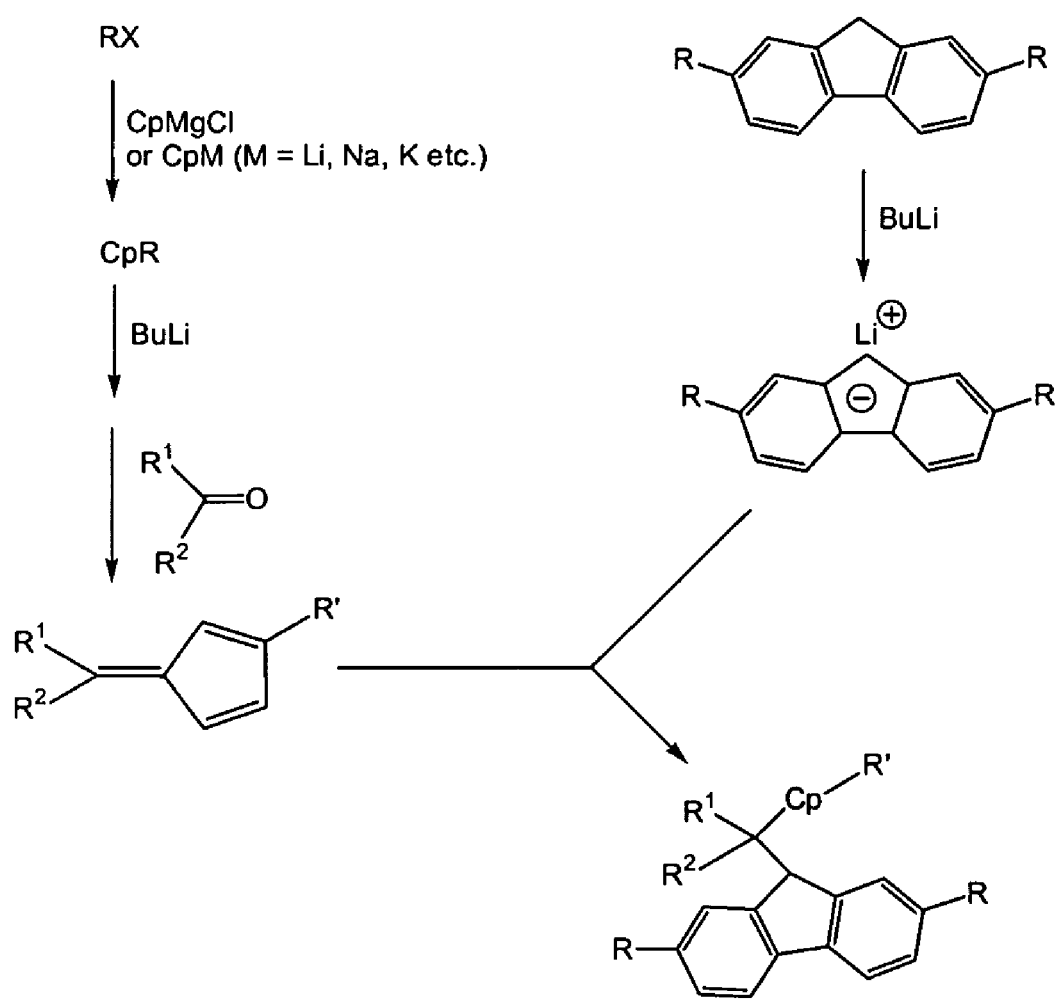
FIG. 1 illustrates a general approach for preparation of ligands for metallocenes M-I and M-II.

In general, ligands for metallocene M-I have been prepared by a multi-step synthesis as illustrated in FIG. 1. By simplifying the synthetic approach to produce such ligands, there would be a resulting cost savings benefit. As discussed above, Alt et al. reported one-pot synthesis for the ligands for metallocene M-II below. Scheme 1 below is the synthesis scheme discussed by Alt et al. Notably, the reactions steps in Scheme 1 occur in the presence of diethyl ether.

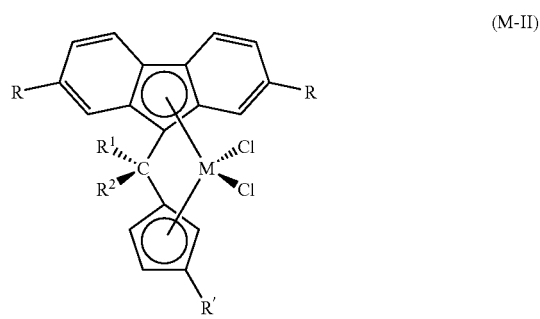

M=Zr, Hf; $R^1=R^2\neq Ph$

Scheme 1: One-Pot Synthesis of Ligands for M-II According to Alt et al.

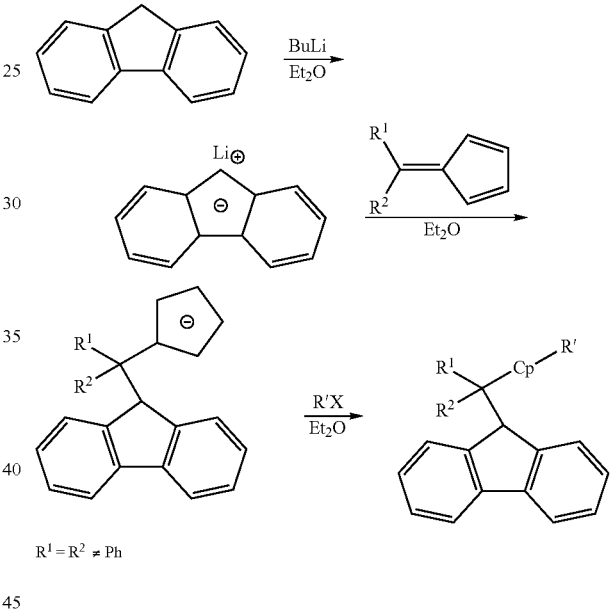

$R^1 = R^2 \neq Ph$

An advantage of this one-pot synthesis is that of fewer synthetic and isolation steps compared to the approach in FIG. 1. In addition, it is more convenient to prepare various analogs with different substituents on the cyclopentadienyl ring via the one-pot synthesis described in Scheme 1. However, we were unable to prepare ligand L-I, below, for metallocene M-I by following the experiments described by Alt et al. Rather, when we followed Alt et al.'s method, undesired ligand L-II, below, was produced at 80-90% isolated yield.

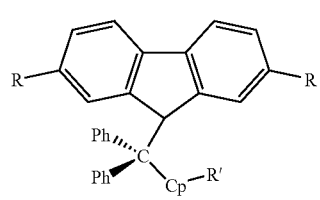

L-I

-continued

L-II

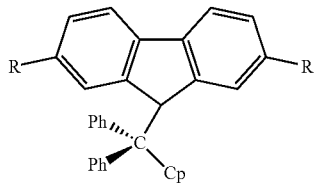

Yet, ligand L-1 can be prepared via a one-pot synthesis when the three steps in Scheme 1 are conducted in the presence of tetrahydrofuran (THF), instead of diethyl ether.

Thus, in accordance with the present invention, a method of making a ligand or compound having structure (I):

(I)

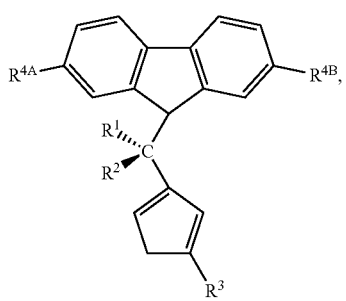

mixture of isomers comprises:

reacting

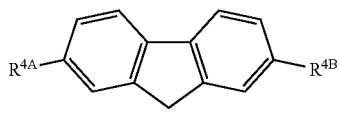

with a lithium compound in the presence of tetrahydrofuran to form (Compound 1)

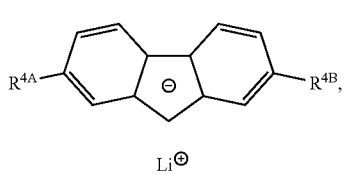

reacting Compound 1 with

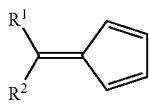

in the presence of tetrahydrofuran to form (Compound 2)

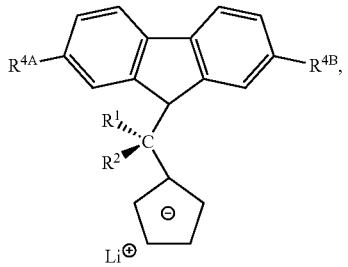

and reacting Compound 2 with $R^3X$ to form the compound of structure (I), wherein $R^1$ and $R^2$ are independently a substituted or unsubstituted phenyl group; $R^3$ is an alkyl, an alkenyl or a substituted silyl, any of which having up to 20 carbon atoms. $R^{4A}$ and $R^{4B}$ are independently a hydrocarbyl group having up to 12 carbon atoms, or hydrogen; X is fluorine, chlorine, bromine, iodine, or para-toluenesulfonate. The lithium compound can be an organic lithium complex, such as methyl lithium, n-butyl lithium, sec-butyllithium, tert-butyllithium and lithium diisopropylamide.

In another aspect of the present invention, a method is disclosed for making a metallocene having the structure:

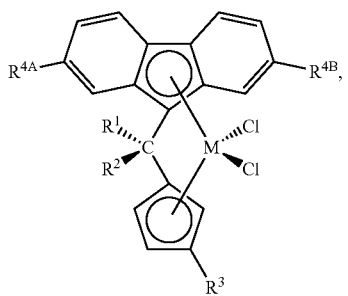

wherein $R^1$ and $R^2$ are independently a substituted or unsubstituted phenyl group; $R^3$ is an alkyl, an alkenyl or a substituted silyl, any of which having up to 20 carbon atoms. $R^{4A}$ and $R^{4B}$ are independently a hydrocarbyl group having up to 12 carbon atoms, or hydrogen; M is Zr or Hf. The method comprises:

reacting

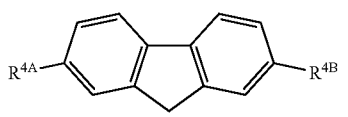

with a lithium compound in the presence of tetrahydrofuran to form (Compound 1)

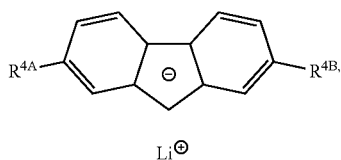

reacting Compound 1 with

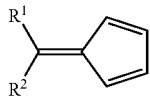

in the presence of tetrahydrofuran to form (Compound 2)

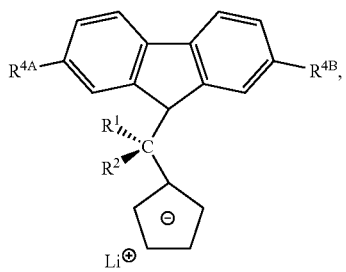

reacting Compound 2 with $R^3X$ to form the compound of structure (I):

(I)

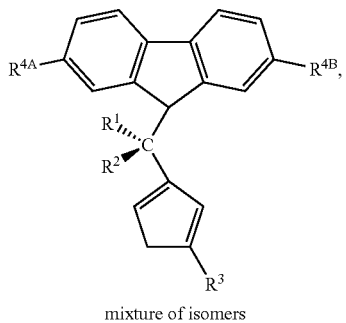

mixture of isomers and reacting the compound of structure (I) with butyllithium to form the dianion (I-dianion)

(I-dianion)

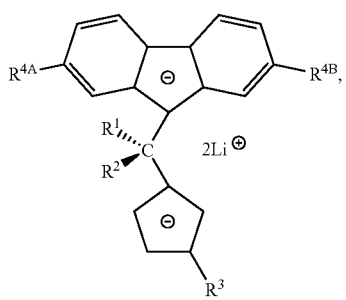

Reacting the dianion (I-dianion) with $MCl_4$ to form the metallocene, where $R^1$, $R^2$, $R^3$, $R^{4A}$, $R^{4B}$, M, and X are as defined above. In the method of the present invention for making the ligand, the lithium compound is an organic lithium complex, such as n-butyl lithium or methyl lithium. Further, in accordance with methods of the present invention, $R^3$ is a linear alkyl group or a linear alkenyl group, any of which having up to 20 carbon atoms, a trimethylsilyl group, a trimethylsilylmethyl group or an allyldimethylsilyl group. Further, in accordance with methods of the present invention, $R^3$ is a butyl group, a pentyl group, a hexyl group or an octyl group. Further, in accordance with methods of the present invention, $R^3$ is a butenyl group, a pentenyl group, a hexenyl group or an octenyl group. In another aspect of the methods of the present invention, $R^{4A}$ and $R^{4B}$ are independently a hydrocarbyl group having up to 6 carbon atoms or hydrogen. Still, in another aspect of the methods of the present invention, $R^{4A}$ and $R^{4B}$ are t-butyl. Yet, in another aspect of the methods of the present invention, $R^{4A}$ and $R^{4B}$ can be such cyclic groups such that the fluorene is octamethyloctahydrodibenzofluorene. See S. A. Miller and J. E. Bercaw, *Organometallics* 23(8), 1777-1789, (2004).

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

For any particular compound disclosed herein, any general structure presented also encompasses all conformational isomers, regioisomers, stereoisomers, and the like, that can arise from a particular set of substituents. The general structure also encompasses all enantiomers, diastereomers, and other optical isomers whether in enantiomeric or racemic forms, as well as mixtures of stereoisomers, as the context requires.

EXAMPLES

The present invention is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, may suggest themselves to one of ordinary skill in the art without departing from the spirit of the present invention or the scope of the appended claims.

In the following examples, unless otherwise specified, the syntheses and preparations described herein were carried out under an inert atmosphere such as nitrogen and/or argon. Solvents were purchased from commercial sources and were typically dried over activated alumina prior to use. Unless otherwise specified, reagents were obtained from commercial sources.

General testing procedures, characterization, and synthetic procedures are provided herein. Synthetic methods to prepare the metallocenes and other reagents of this invention are also provided herein.

Reagents

Unless specified otherwise, reagents were obtained from Aldrich Chemical Company and used without further purification. 2,7-di-tert-butylfluorene was purchased from Degussa Corporation, Parsippany. N.J. Tetrahydrofuran (THF) was distilled from potassium metal under nitrogen. Anhydrous diethylether, methylene chloride and n-pentane were degassed and dried over activated alumina. 6,6-diphenylpentafulvene is commercially available from Aldrich Chemical Company.

A general procedure for metallocene preparation is as follows: To the ligand dissolved or suspended in $Et_2O$ was slowly added 2.1 equivalents of n-BuLi at 0° C. The mixture was warmed to room temperature, stirred overnight, and then added via a cannula to 1.1 equivalent of $HfCl_4$ suspended in a mixture of pentane and $Et_2O$ at 0° C. The mixture was warmed to room temperature and stirred overnight. The solvent was removed. The residue was mixed with pentane and centrifuged. The liquid was decanted off. The remaining solid was washed a second time with pentane, then extracted with methylene chloride and centrifuged. The solution was taken to dryness under vacuum to give the corresponding metallocene. Nuclear Magnetic Resonance (NMR) spectra were obtained on a Varian Mercury Plus 300 NMR spectrometer operating at 300 MHz for $^1H$ NMR ($CDCl_3$ solvent, referenced against the peak of residual $CHCl_3$ at 7.24 ppm).

Comparative Example 1

Figure 2:
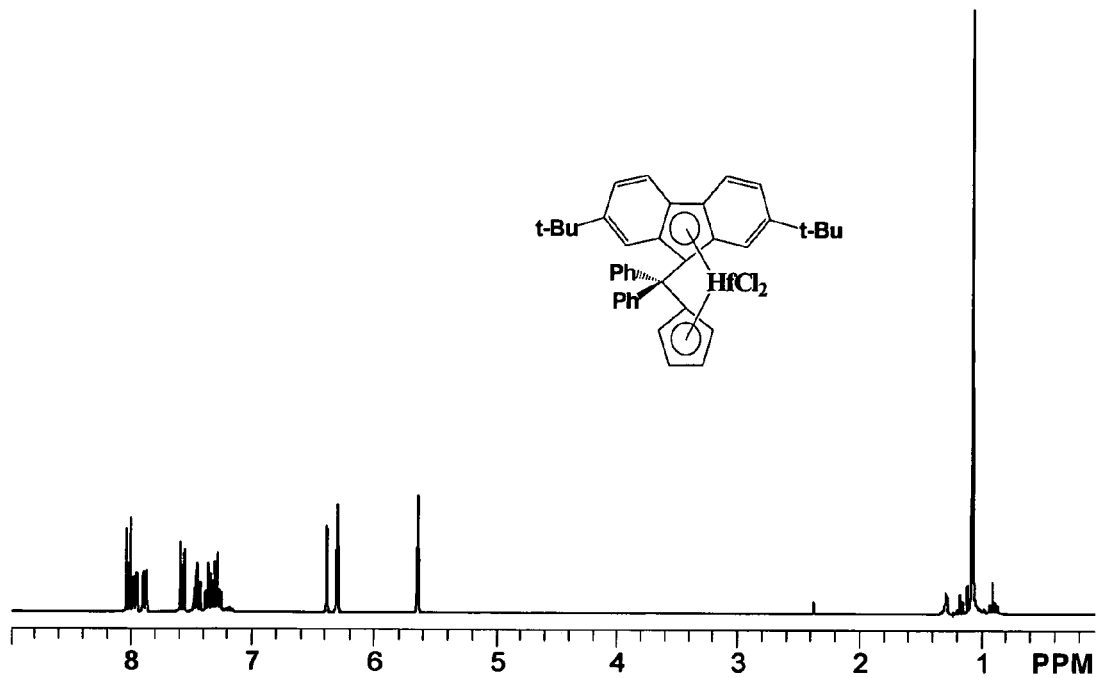
FIG. 2 is a $^1$H-NMR plot for illustration of the metallocene made from the ligand of Comparative Example 1.

To 2,7-di-tert-butylfluorene (5.6 g, 20 mmol) dissolved in $Et_2O$ (30 mL) was added n-BuLi (2.1 mL of 10 M in hexanes, 21 mmol) at 0° C. The mixture was warmed to room temperature and stirred overnight. To above anion solution was added 6,6-diphenylpentafulvene (4.8 g, 21 mmol) dissolved in $Et_2O$ (20 mL) at 0° C. The mixture was warmed to room temperature and stirred for about 7 hours. To above reaction mixture was added 5-bromo-1-pentene (3.77 g of 95 wt %, 24 mmol) at 0° C. The mixture was warmed to room temperature and stirred overnight. The reaction was quenched with a mixture of ice and 10% HCl aqueous solution. The mixture was extracted with $Et_2O$. The organic layer was washed with water and dried over anhydrous sodium sulfate. Removal of the solvent under vacuum gave a yellow solid. The solid was washed with heptane and dried under vacuum. A mixture of isomers for ligand L-II, where R is t-butyl, (8.4 g, 82.7% yield) was obtained as a white solid. MS: m/e 508 ($M^+$). Thus, no addition to the cyclopentadienyl ring occurred. The ligand was also confirmed by being converted to the corresponding metallocene by reacting the ligand dianion with $HfCl_4$. (FIG. 2).

Comparative Example 2

Figure 3:
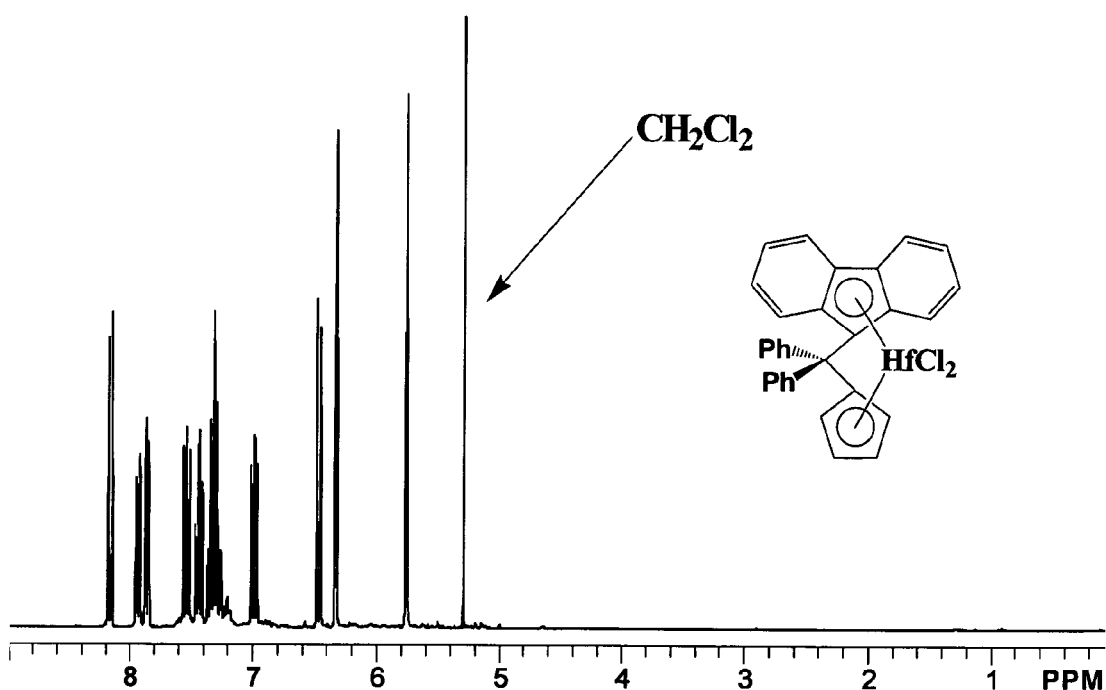
FIG. 3 is a $^1$H-NMR plot for illustration of the metallocene made from the ligand of Comparative Example 2.

To fluorene (3.32 g, 20 mmol) dissolved in $Et_2O$ (40 mL) was added n-BuLi (2.1 mL of 10 M in hexanes, 21 mmol) at 0° C. The mixture was warmed to room temperature and stirred overnight. To above anion solution was added 6,6-diphenylpentafulvene (4.8 g, 21 mmol) dissolved in $Et_2O$ (20 mL) at 0° C. The mixture was warmed to room temperature and stirred overnight. To above reaction mixture was added 5-bromo-1-pentene (3.46 g of 95 wt %, 22 mmol) at 0° C. The mixture was warmed to room temperature and stirred overnight. The reaction was quenched with a mixture of ice and 10% HCl aqueous solution. The mixture was extracted with $CH_2Cl_2$. The organic layer was washed with water and dried over anhydrous sodium sulfate. Removal of the solvent under vacuum gave a yellow solid. The solid was washed with heptane and dried under vacuum. A mixture of isomers for ligand L-II, where R is hydrogen, (7.1 g, 89.6% yield) was obtained as a pale yellow solid. MS: m/e 396 ($M^+$). Thus, no addition to the cyclopentadienyl ring occurred. The ligand was also confirmed by being converted to the corresponding metallocene. (FIG. 3).

Comparative Example 3

Figure 4:
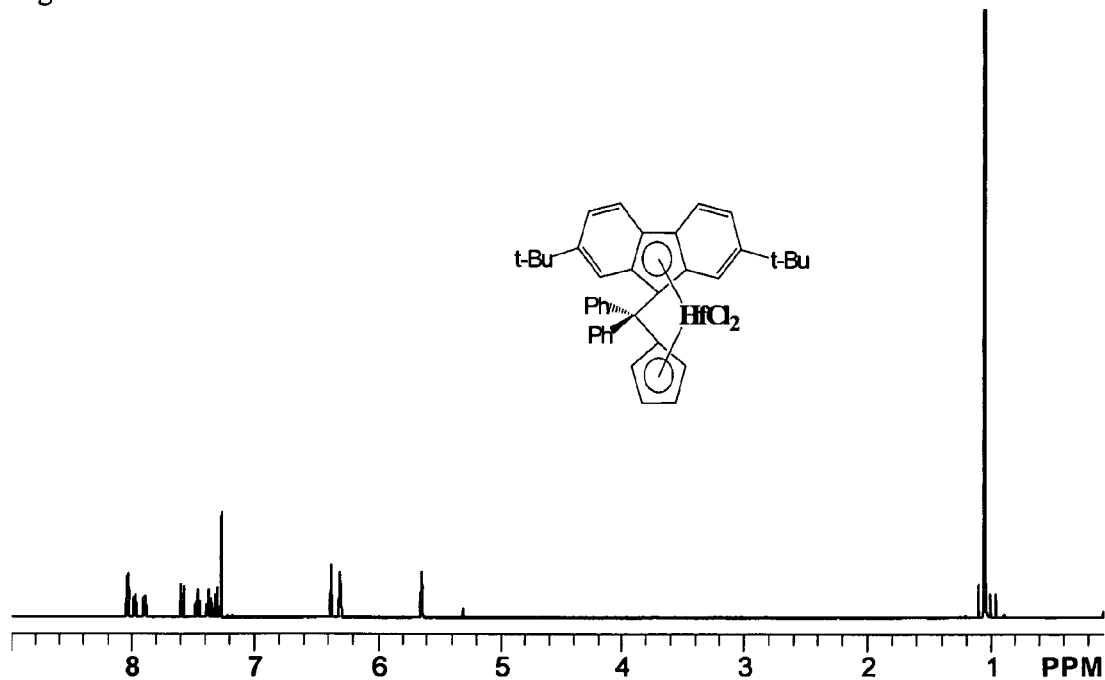
FIG. 4 is a $^1$H-NMR plot for illustration of the metallocene made from the ligand of Comparative Example 3.

To 2,7-di-tert-butylfluorene (5.6 g, 20 mmol) dissolved in $Et_2O$ (30 mL) was added n-BuLi (2.1 mL of 10 M in hexanes, 21 mmol) at 0° C. The mixture was warmed to room temperature and stirred overnight. To above anion solution was added 6,6-diphenylpentafulvene (4.8 g, 21 mmol) dissolved in $Et_2O$ (20 mL) at 0° C. The mixture was warmed to room temperature and stirred overnight. To above reaction mixture was added 5-bromo-1-pentene (3.46 g of 95 wt %, 22 mmol) at room temperature. The mixture was heated at 55° C. for about 4 hours. The reaction was quenched with a mixture of ice and 10% HCl aqueous solution. The mixture was extracted with $CH_2Cl_2$. The organic layer was washed with water and dried over anhydrous sodium sulfate. Removal of the solvent under vacuum gave a brown solid. The solid was washed with heptane and dried under vacuum. A mixture of isomers for ligand L-II, where R is t-butyl, (8.4 g, 82.7% yield) was obtained as a pale yellow solid. MS: m/e 508 ($M^+$). Thus, no addition to the cyclopentadienyl ring occurred. The ligand was also confirmed by being converted to the corresponding metallocene. (FIG. 4).

Inventive Example 4

Figure 5:
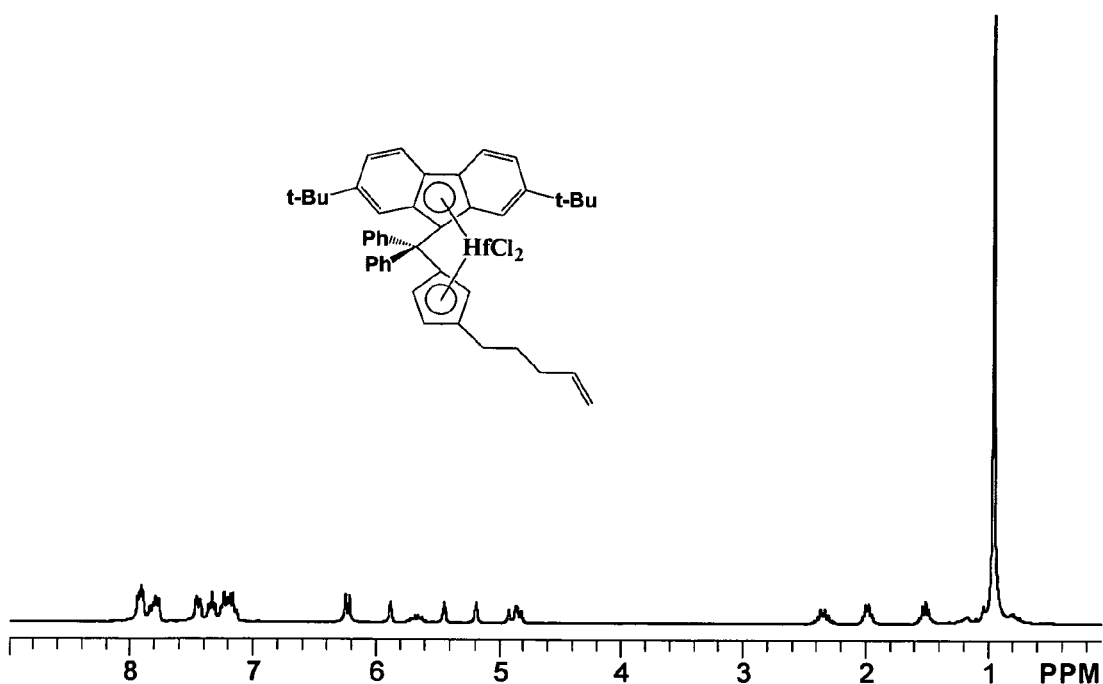
FIG. 5 is a $^1$H-NMR plot for illustration of the metallocene made from the ligand of Inventive Example 4.

To 2,7-di-tert-butylfluorene (5.6 g, 20 mmol) dissolved in THF (30 mL) was added n-BuLi (2.1 mL of 10 M in hexanes, 21 mmol) at −78° C. The mixture was warmed to room temperature and stirred overnight. To above anion solution was added 6,6-diphenylpentafulvene (4.8 g, 21 mmol) dissolved in THF (20 mL) at 0° C. The mixture was warmed to room temperature and stirred for about 8 hours. To above reaction mixture was added 5-bromo-1-pentene (3.46 g of 95 wt %, 22 mmol) at 0° C. The mixture was warmed to room temperature and stirred overnight. The reaction was quenched with a mixture of ice-water. The mixture was extracted with $Et_2O$. The organic layer was washed with saturated $NH_4Cl$ and water, then dried over anhydrous sodium sulfate. Removal of the solvent under vacuum gave a viscous brown oil as crude product. The crude product was purified by column chromatography with 5-10% $CH_2Cl_2$ in heptane. A mixture of isomers for desired ligand of structure (I), where $R^{4A}$ and $R^{4B}$ are t-butyl, $R^3$ is pentenyl (9.2 g, 79% yield) was obtained. MS: m/e 576 ($M^+$). The ligand was also confirmed by being converted to the corresponding metallocene. (FIG. 5).

Inventive Example 5

To 2,7-di-tert-butylfluorene (5.6 g, 20 mmol) dissolved in THF (30 mL) was added n-BuLi (2.1 mL of 10 M in hexanes, 21 mmol) at −78° C. The mixture was warmed to room temperature and stirred overnight. To above anion solution was added 6,6-diphenylpentafulvene (4.8 g, 21 mmol) dissolved in THF (20 mL) at 0° C. The mixture was warmed to room temperature and stirred overnight. To above reaction mixture was added 5-bromo-1-pentene (3.46 g of 95 wt %, 22 mmol) at room temperature. The mixture was refluxed at 70° C. for about 3 hours. The reaction was quenched with a mixture of ice-water. The mixture was extracted with $Et_2O$.

Figure 6:
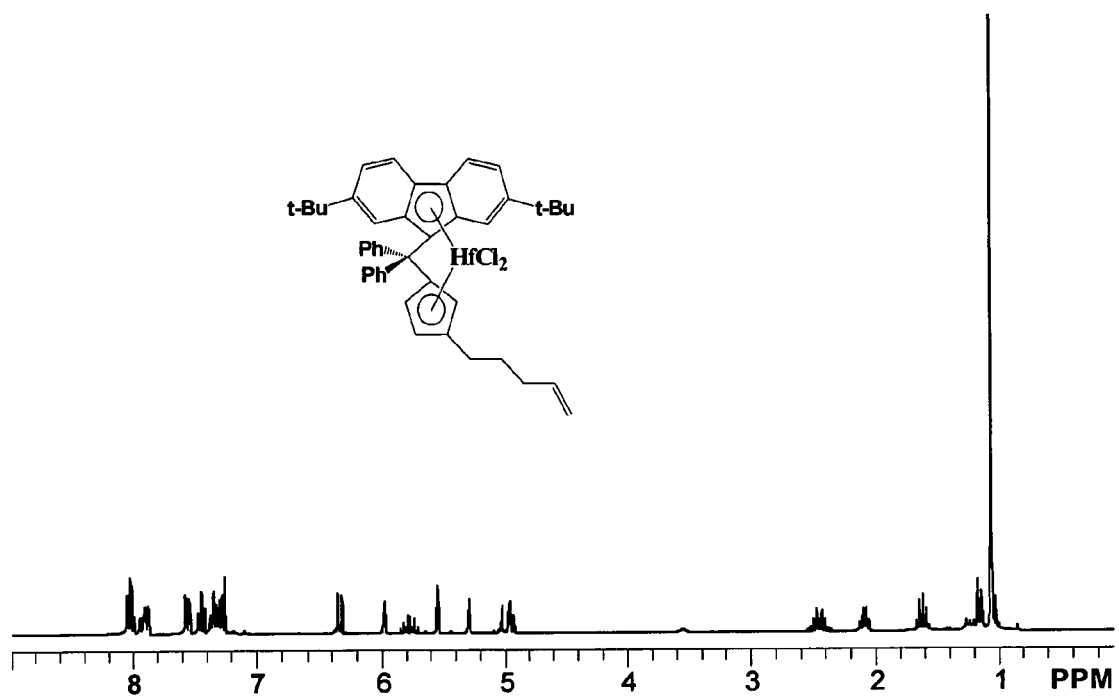
FIG. 6 is a $^1$H-NMR plot for illustration of the metallocene made from the ligand of Inventive Example 5.

The organic layer was washed with saturated NH$_4$Cl and water, then dried over anhydrous sodium sulfate. Removal of the solvent under vacuum gave a viscous brown oil as crude product. The crude product was purified by column chromatography with 5-10% CH$_2$Cl$_2$ in heptane. A mixture of isomers for desired ligand of structure (I), where R$^{4A}$ and R$^{4B}$ are t-butyl, R$^3$ is pentenyl (8.3 g, 72% yield) was obtained. MS: m/e 576 (M$^+$). The ligand was also confirmed by being converted to the corresponding metallocene. (FIG. 6).

What is claimed is:

1. A method of making a compound having structure (I):

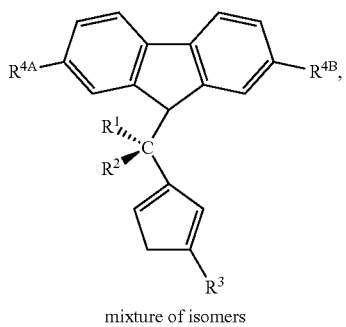

(I)

mixture of isomers the method comprising:
reacting

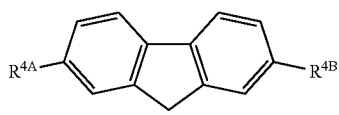

with a lithium compound in the presence of tetrahydrofuran, an alkyl or aryl substituted tetrahydrofuran, tetrahydropyran, an alkyl or aryl substituted tetrahydropyran or ethylene glycol dimethyl ether to form

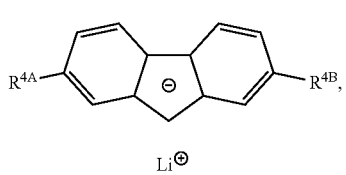

(Compound 1)

reacting Compound 1 with

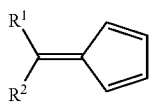

in the presence of tetrahydrofuran, an alkyl or aryl substituted tetrahydrofuran, tetrahydropyran, an alkyl or aryl substituted tetrahydropyran or ethylene glycol dimethyl ether to form

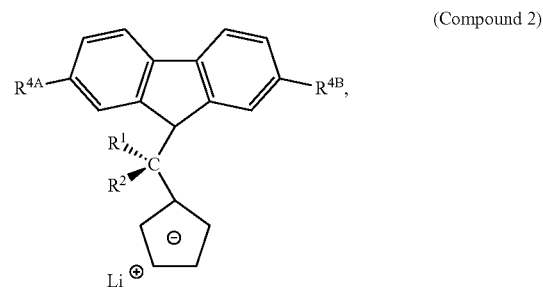

(Compound 2)

and reacting Compound 2 with R$^3$X to form the compound of structure (I), wherein:
R$^1$ and R$^2$ are independently a substituted or unsubstituted phenyl group;
R$^3$ is an alkyl, an alkenyl or a substituted silyl group, any of which having up to 20 carbon atoms;
R$^{4A}$ and R$^{4B}$ are independently a hydrocarbyl group having up to 12 carbon atoms, or hydrogen;
X is fluorine, chlorine, bromine, iodine, or para-toluenesulfonate.

2. The method according to claim 1, wherein the lithium compound is an organo lithium.

3. The method according to claim 1, wherein R$^3$ is a linear alkyl group or a linear alkenyl group having up to 10 carbon atoms, trimethylsilyl group or allyldimethylsilyl group.

4. The method according to claim 1, wherein R$^{4A}$ and R$^{4B}$ are independently a hydrocarbyl group having up to 6 carbon atoms or hydrogen.

5. The method according to claim 1, wherein R$^3$ is a linear terminal alkenyl group having up to 10 carbon atoms.

6. The method according to claim 1, wherein R$^{4A}$ and R$^{4B}$ are t-butyl.

7. A method of making a metallocene having the structure:

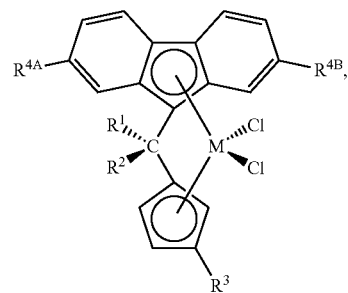

the method comprising:
reacting

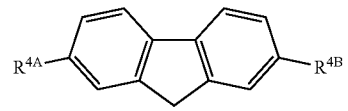

with a lithium compound in the presence of tetrahydrofuran, a substituted tetrahydrofuran, tetrahydropyran, a substituted tetrahydropyran or ethylene glycol dimethyl ether to form

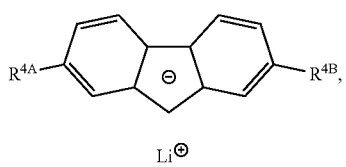

(Compound 1)

reacting Compound 1 with

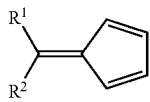

in the presence of tetrahydrofuran, a substituted tetrahydrofuran, tetrahydropyran, a substituted tetrahydropyran or ethylene glycol dimethyl ether to form

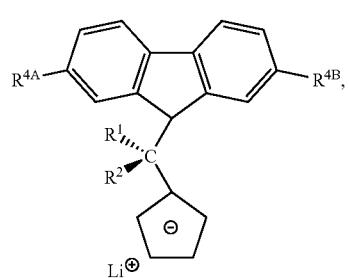

(Compound 2)

reacting Compound 2 with $R^3X$ to form the compound of structure (I):

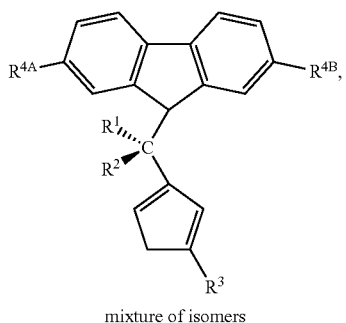

(I)

mixture of isomers reacting the compound of structure (I) with butyllithium to form the dianion (I-dianion)

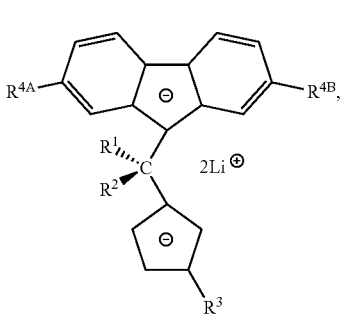

(I-dianion)

and reacting the dianion (I-dianion) with $MCl_4$ to form the metallocene;

wherein:

$R^1$ and $R^2$ are independently an alkyl group or an aryl group, either of which having up to 10 carbon atoms, or hydrogen;

$R^3$ is an alkyl, an alkenyl or a substituted silyl group, any of which having up to 20 carbon atoms;

$R^{4A}$ and $R^{4B}$ are independently a hydrocarbyl group having up to 12 carbon atoms, or hydrogen;

X is fluorine, chlorine, bromine, iodine, or para-toluenesulfonate;

M is Zr or Hf.

8. The method according to claim 7, wherein the lithium compound is selected from methyl lithium, n-butyl lithium, sec-butyllithium, tert-butyllithium and lithium diisopropylamide.

9. The method according to claim 7, wherein $R^3$ is a linear alkyl group or a linear alkenyl group having up to 10 carbon atoms, trimethylsilyl group or allyldimethylsilyl group.

10. The method according to claim 7, wherein $R^{4A}$ and $R^{4B}$ are independently a hydrocarbyl group having up to 6 carbon atoms or hydrogen.

11. The method according to claim 7, wherein $R^3$ is a linear terminal alkenyl group having up to 10 carbon atoms.

12. The method according to claim 10, wherein $R^{4A}$ and $R^{4B}$ are t-butyl.

* * * * *